US012594138B2

(12) United States Patent (10) Patent No.: US 12,594,138 B2
Morita et al. (45) Date of Patent: Apr. 7, 2026

(54) BEARING STRUCTURE AND DRAPE UNIT INCLUDING BEARING STRUCTURE

(71) Applicant: RIVERFIELD INC., Tokyo (JP)

(72) Inventors: Naoya Morita, Tokyo (JP); Nobuaki Kurihara, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 747 days.

(21) Appl. No.: 17/953,679

(22) Filed: Sep. 27, 2022

(65) Prior Publication Data

US 2023/0016675 A1 Jan. 19, 2023

Related U.S. Application Data

(63) Continuation of application No. PCT/JP2020/015234, filed on Apr. 2, 2020.

(51) Int. Cl.
| | |
|---|---|
| *A61B 46/10* | (2016.01) |
| *A61B 34/30* | (2016.01) |
| *A61B 46/00* | (2016.01) |
| *A61B 90/00* | (2016.01) |

(52) U.S. Cl.
CPC .............. *A61B 46/10* (2016.02); *A61B 34/30* (2016.02); *A61B 46/40* (2016.02); *A61B 90/08* (2016.02); *A61B 2090/0808* (2016.02)

(58) Field of Classification Search
CPC ......... A61B 46/10; A61B 46/23; A61B 50/00; A61B 50/30; A61B 90/20; A61B 90/50;
A61B 34/30; A61B 34/35; A61B 2017/00477; A61B 34/32; A61B 34/70; A61B 34/71; A61B 90/10; A61B 90/11; A61B 17/068
See application file for complete search history.

(56) References Cited

U.S. PATENT DOCUMENTS

| | | | |
|---|---|---|---|
| 3,698,791 A | 10/1972 | Walchle et al. | |
| 5,467,223 A * | 11/1995 | Cleveland, Jr. .... | G02B 21/0012 |
| | | | 359/511 |

(Continued)

FOREIGN PATENT DOCUMENTS

| | | | | |
|---|---|---|---|---|
| EP | 4 389 056 A1 * | 6/2024 | ............. | A61B 46/10 |
| JP | 2003-220077 A | 8/2003 | | |

(Continued)

OTHER PUBLICATIONS

European Search Report dated Mar. 17, 2023 in Application No. 20928986.7.

(Continued)

*Primary Examiner* — Camtu T Nguyen
(74) *Attorney, Agent, or Firm* — Sughrue Mion, PLLC

(57) ABSTRACT

A bearing structure includes a fixing member attached with respect to an arm of a surgical robot in a state in which a holder that is provided at a distal end of the arm is inserted inside the fixing member, a first drape that covers the arm being attachable to the fixing member, and a rotating member attached with respect to the fixing member in a slidably rotatable manner in a state in which the holder is inserted inside the rotating member, a second drape that covers the holder being attachable to the rotating member. The rotating member is rotatable together with the holder.

23 Claims, 14 Drawing Sheets

(56) References Cited

U.S. PATENT DOCUMENTS

| | | | | |
|---|---|---|---|---|
| 5,792,045 | A * | 8/1998 | Adair | A61B 1/00128 |
| | | | | 600/125 |
| 6,063,095 | A * | 5/2000 | Wang | A61B 34/37 |
| | | | | 606/139 |
| 6,375,610 | B2 * | 4/2002 | Verschuur | A61B 46/10 |
| | | | | 600/125 |
| 7,122,032 | B2 * | 10/2006 | Shinmura | A61B 90/36 |
| | | | | 606/34 |
| 11,571,195 | B2 * | 2/2023 | Beira | B25J 19/0075 |
| 12,290,333 | B2 * | 5/2025 | Bernstein | A61B 34/30 |
| 2019/0167365 | A1 | 6/2019 | Chaplin et al. | |

FOREIGN PATENT DOCUMENTS

| | | | |
|---|---|---|---|
| JP | 2006-102224 | A | 4/2006 |
| JP | 5193049 | B2 | 2/2013 |
| JP | 2019-521736 | A | 8/2019 |
| JP | 2019-523072 | A | 11/2019 |
| WO | 2009/092701 | A1 | 7/2009 |
| WO | 2017/015207 | A | 1/2017 |
| WO | 2017-041093 | A1 | 3/2017 |
| WO | 2016/051494 | A1 | 4/2017 |
| WO | 2019/150111 | A1 | 8/2019 |

OTHER PUBLICATIONS

Communication dated Mar. 29, 2023, from the European Patent Office in Application No. 20928986.7.

International Search Report of PCT/JP2020/015234 dated Jun. 9, 2020.

Written Opinion for International Application PCT/JP2020/015234 dated Jun. 9, 2020.

* cited by examiner

BEARING STRUCTURE AND DRAPE UNIT INCLUDING BEARING STRUCTURE

CROSS REFERENCE TO RELATED APPLICATIONS

This U.S. application is a continuation application of International Application No. PCT/JP2020/015234 filed Apr. 2, 2020, in the Japanese Patent Office, the contents of which being incorporated by reference herein in its entirety.

BACKGROUND

The present disclosure relates to a bearing structure for a drape that covers a surgical robot including a holder for holding an insertion member and relates also to a drape unit including the bearing structure.

A surgical robot may be provided with a sterile drape that covers a portion of the surgical robot in order to protect a patient from non-sterile portions of the surgical robot during surgery. However, an arm of the surgical robot or an insertion member that is inserted into the patient during surgery and is attached to the tip of the arm may be rotated, and in such a case, the drape may be twisted.

SUMMARY

It is an aspect to provide a bearing structure for a drape that covers a surgical robot and that is capable of reducing the possibility that the drape is broken even when there is a rotation operation such that the relative angle exceeds 360 degrees and also that is capable of reliably maintaining the separation between a clean area and an unclean area.

It is another aspect to provide a drape unit including such a bearing structure.

According to an aspect of one or more embodiments, there is provided a bearing structure comprising a fixing member attached with respect to an arm of a surgical robot in a state in which a holder that is provided at a distal end of the arm is inserted inside the fixing member, a first drape that covers the arm being attachable to the fixing member; and a rotating member attached with respect to the fixing member in a slidably rotatable manner in a state in which the holder is inserted inside the ring-shaped rotating member, a second drape that covers the holder being attachable to the rotating member, wherein the rotating member is rotatable together with the holder.

According to another aspect of one or more embodiments, there is provided a drape unit comprising the bearing structure; the first drape attached to the fixing member; the second drape attached to the rotating member; and a separator that is connected to the second drape, wherein the holder detachably holds an insertion member that is inserted into a patient during a surgery, and the separator is located between the holder and the insertion member.

According to yet another aspect of one or more embodiments, there is provided a bearing structure comprising a fixing member that is attached through a bearing member to a holding body provided at a distal end of an arm of a surgical robot, the fixing member comprising an annular groove in an outer circumferential surface at a distal end of the fixing member, a first drape that covers the arm being attachable to the fixing member; and a rotating member that comprises a plurality of tongue protrusions that protrude radially inward at a distal end of the rotating member, a second drape being attachable to the rotating member, wherein, when the rotating member is fitted to the fixing member, the plurality of tongue protrusions engage with the annular groove such that the plurality of tongue protrusions are rotatable within the annular groove.

BRIEF DESCRIPTION OF THE DRAWINGS

The above and/or other aspects will become apparent and more readily appreciated from the following description of exemplary embodiments, taken in conjunction with the accompanying drawings in which:

FIG. 8A is a side view illustrating a state before attaching a drape unit and FIG. 8B is a side view illustrating a state in which the drape unit is attached to the holding body side;

FIG. 9A is a plan view as viewed along the direction of an axis of rotation and FIG. 9B is a perspective view;

DETAILED DESCRIPTION

Figure 1:
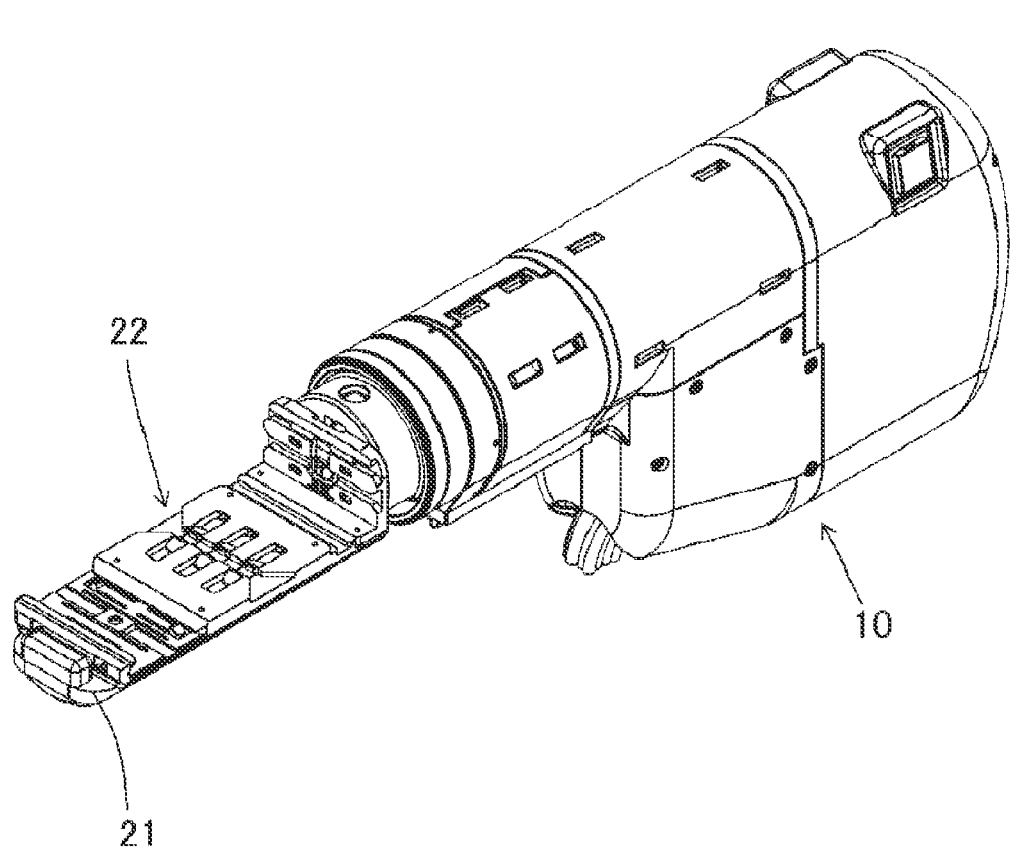
FIG. 1 is a perspective view illustrating an external configuration of a holding body of a medical robot including a bearing structure according to some embodiments.

A sterile drape for a surgical procedure may include, for example, an exterior surface adjacent to a sterile field for performing the surgical procedure, an interior surface forming a cavity for receiving a non-sterile portion of a robotic surgical system, an integral cuff including a permanently folded cease of the above exterior surface and the above interior surface at an open end of the cavity and a marker on the permanently folded cease that specifies a sterile side and a non-sterile side of the drape, and a fastener for securing the above sterile drape to the above non-sterile portion while reducing the volume of the sterile drape. With such a configuration, it may be possible to increase visualization of the patient by reducing the size of the drape, allow for quick and simple installation, and improve the instrument sterile adaptor feature.

In the treatment, however, the arm unit of a robot or the insertion member attached to the tip of the arm unit may be rotated, and in such a case, the drape may be twisted because the relative angle between the arm unit with the drape and the insertion member without the drape is changed. In particular, in recent years, there are cases in which the above relative angle exceeds 360 degrees. In such cases, the drape may be broken by a large twist, and the robot's operation may be hindered, resulting in malfunction or narrowing of the movable range.

It is an aspect to provide a bearing structure for a drape that covers a surgical robot, the bearing structure capable of reducing the possibility that the drape is broken even when there is a rotation operation such that the relative angle exceeds 360 degrees and also capable of reliably maintaining the separation between a clean area and an unclean area. It is another aspect to provide a drape unit including such a bearing structure.

According to some embodiments, there may be provided a bearing structure for a drape that covers a surgical robot having an arm whose tip is provided with a holder that detachably holds an insertion member in a rotatable manner. The bearing structure may include a ring-shaped fixing member attached with respect to the arm in a state in which the holder is inserted inside; and a ring-shaped rotating member attached with respect to the fixing member in a slidably rotatable manner in a state in which the holder is inserted inside. The rotating member may be rotatable together with the holder. The drape may include a first drape that covers the arm and can be attached to the fixing member; and a second drape that covers the holder and can be attached to the rotating member in a rotatable manner together with the rotating member.

In some embodiments, the fixing member may include a ring-shaped base member that is attached with respect to the arm; and a ring-shaped joint member that is detachably attached with respect to the base member by fitting, and the rotating member may be attached with respect to the joint member in a slidably rotatable manner.

In some embodiments, the base member and the joint member may be detachably fitted to each other by fitting a fitting protrusion provided on one of the base member and the joint member and a fitting recess provided in another of the base member and the joint member to each other.

In some embodiments, the fitting protrusion may be provided on an outer circumferential surface of the base member and the fitting recess may be provided in an inner circumferential surface of the joint member, or the fitting protrusion may be provided on the inner circumferential surface of the joint member and the fitting recess may be provided in the outer circumferential surface of the base member.

In some embodiments, the fitting recess may be provided in a linked manner with a guide groove extending along a circumferential direction of the fixing member and the rotating member, and the fitting protrusion may be moved along the guide groove thereby to rotate and guide the joint member with respect to the base member, guiding the fitting protrusion into the fitting recess.

In some embodiments, the guide groove may extend along a main axis direction from a fitting side end portion in the main axis direction and further extend in the circumferential direction of the fixing member and the rotating member. The main axis direction may be an axial direction of the fixing member and the rotating member.

In some embodiments, the guide groove may have a tapered portion in which a depth of the groove decreases as the guide groove extends from its end portion in the main axis direction along the main axis direction.

In some embodiments, the fitting recess and the fitting protrusion may include two or more pairs of fitting recesses and fitting protrusions provided in the circumferential direction of the fixing member and the rotating member, the fitting protrusions may be provided at positions at a predetermined distance in the main axis direction from the fitting side end portion in the main axis direction, and a member provided with the fitting protrusions may be guided to a member provided with the fitting recesses by rotating the member provided with the fitting protrusions while bringing the fitting protrusions into contact with non-fitting regions in which the guide groove is not provided in the fitting side end portion in the main axis direction of the member provided with the fitting recesses.

In some embodiments, the guide groove may be formed to have a wider width than that of the fitting recess in the main axis direction.

In some embodiments, the fitting protrusions may have respective fitting side end portions in the main axis direction, the fitting side end portions may form a plane orthogonal to the main axis direction, and the non-fitting regions may be located on a plane orthogonal to the main axis direction.

In some embodiments, the fitting recess and the fitting protrusion may include two or more pairs of fitting recesses and fitting protrusions provided in a circumferential direction of the fixing member and the rotating member.

In some embodiments, three or more of the fitting recesses and three or more of the fitting protrusions may be provided in the circumferential direction of the fixing member and the rotating member.

In some embodiments, at least some of the fitting recesses and fitting protrusions may have different intervals in the circumferential direction of the fixing member and the rotating member.

In some embodiments, the guide groove may be provided in a linked manner with the fitting recess via a restriction protrusion, and the restriction protrusion may restrict the fitting protrusion fitted in the fitting recess from returning to the guide groove.

In some embodiments, the base member and the joint member may be provided with respective fitting markers that indicate that the fitting protrusion has reached a position at which it is fitted into the fitting recess by rotating the joint member relative to the base member.

In some embodiments, the fitting marker provided on the base member and the fitting marker provided on the joint member may be arranged at a same position as each other in the circumferential direction of the fixing member when the fitting protrusion has reached the position at which it is fitted into the fitting recess.

In some embodiments, the base member may be provided with an initial position marker that indicates a position at which the fitting protrusion is entered into the guide groove.

In some embodiments, the first drape may be fixed to an outer circumferential surface of the joint member, and the base member and the joint member may have a gap having a length that is at least twice a thickness of the first drape in an axial direction of the fixing member and the rotating member.

In some embodiments, the fixing member may have a protruding edge portion that protrudes outward in a radial direction at an end portion of the fixing member in an axial direction, and the rotating member attached to the fixing member in the slidably rotatable manner preferably may come into contact with the protruding edge portion thereby to be prevented from coming off from the fixing member.

In some embodiments, the rotating member may have a tongue portion that protrudes outward in the radial direction at an end portion of the rotating member in the axial direction, the fixing member may have a groove portion recessed inward adjacent to the protruding edge portion in the axial direction, and the tongue portion may engage with the groove portion.

In some embodiments, the base member may be composed of a metal, and the joint member and the rotating member are preferably composed of a resin material having durability against sterilization.

In some embodiments, the fitting protrusion may have a shape that protrudes in a hemispherical shape.

In some embodiments, the fitting protrusion may have a spherical portion and a biasing portion that biases the spherical portion in an outward direction.

According to some embodiments, there may be provided a drape unit including: any form of the bearing structure as described above, the first drape may be attached to the fixing member, the second drape may be attached to the rotating member, and a separator that is provided in a linked manner with the second drape and may be located between the insertion member and the holder to cover the holder.

According to various embodiments, not only when the relative angle of the insertion member with respect to the arm unit is less than 360 degrees, but also when the insertion member is operated to rotate so as to exceed 360 degrees, it is possible to reduce the possibility that the drape which covers the rotating member, the fixing member, the holding body, the arm unit, etc. is broken and also to reliably maintain the separation between a clean area and an unclean area.

Hereinafter, the bearing structure according to some embodiments will be described in detail with reference to the drawings. An example will be described in which the bearing structure is applied to a medical robot, but embodiments are not limited to this.

In each figure, X-Y-Z coordinates are illustrated as reference coordinates. In the following description, the Z1-Z2 direction is referred to as an up-down direction, the X1-X2 direction is referred to as a front-rear direction, and the Y1-Y2 direction is referred to as a left-right direction. The X1-X2 direction and the Y1-Y2 direction are orthogonal to each other, and the X-Y plane including the X1-X2 direction and the Y1-Y2 direction is orthogonal to the Z1-Z2 direction. In the following description, a state in which the lower side (Z2 side) is viewed from the upper side (Z1 side) may be referred to as a plan view.

(Overall Structure)

Figure 2:
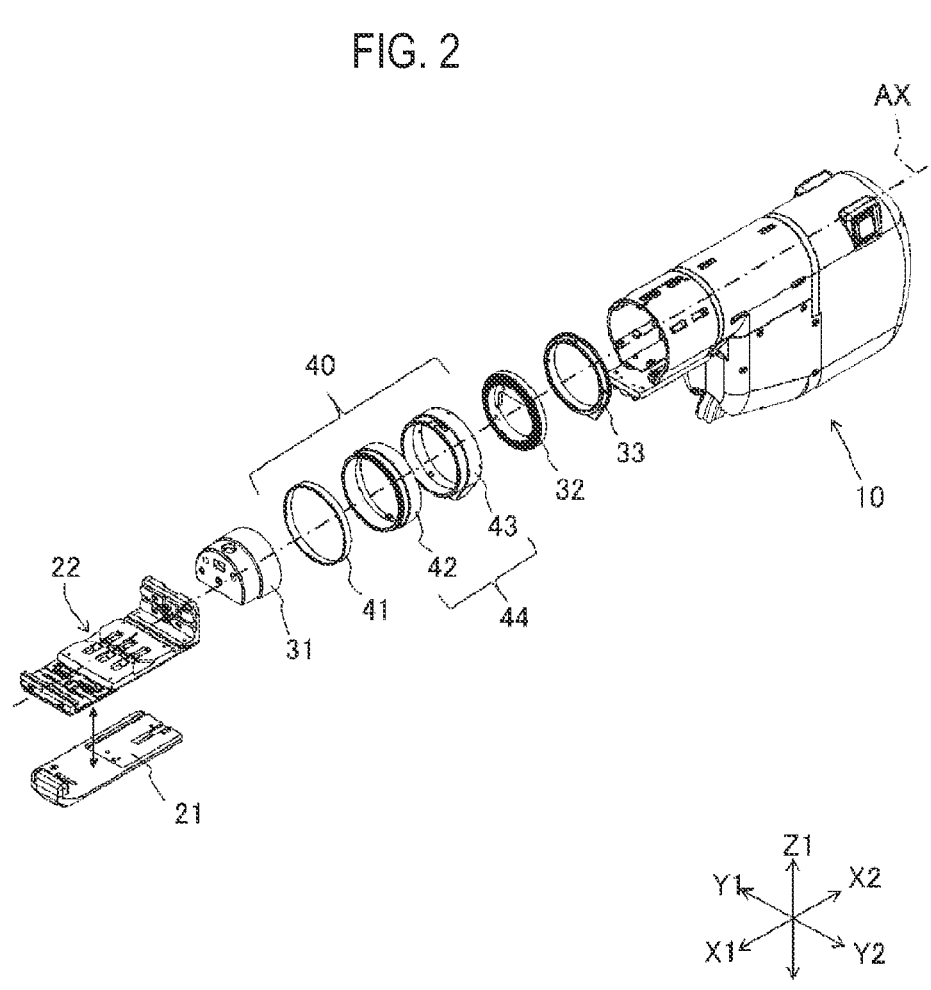
FIG. 2 is an exploded perspective view illustrating a schematic configuration of the holding body, according to some embodiments.
Figure 3:
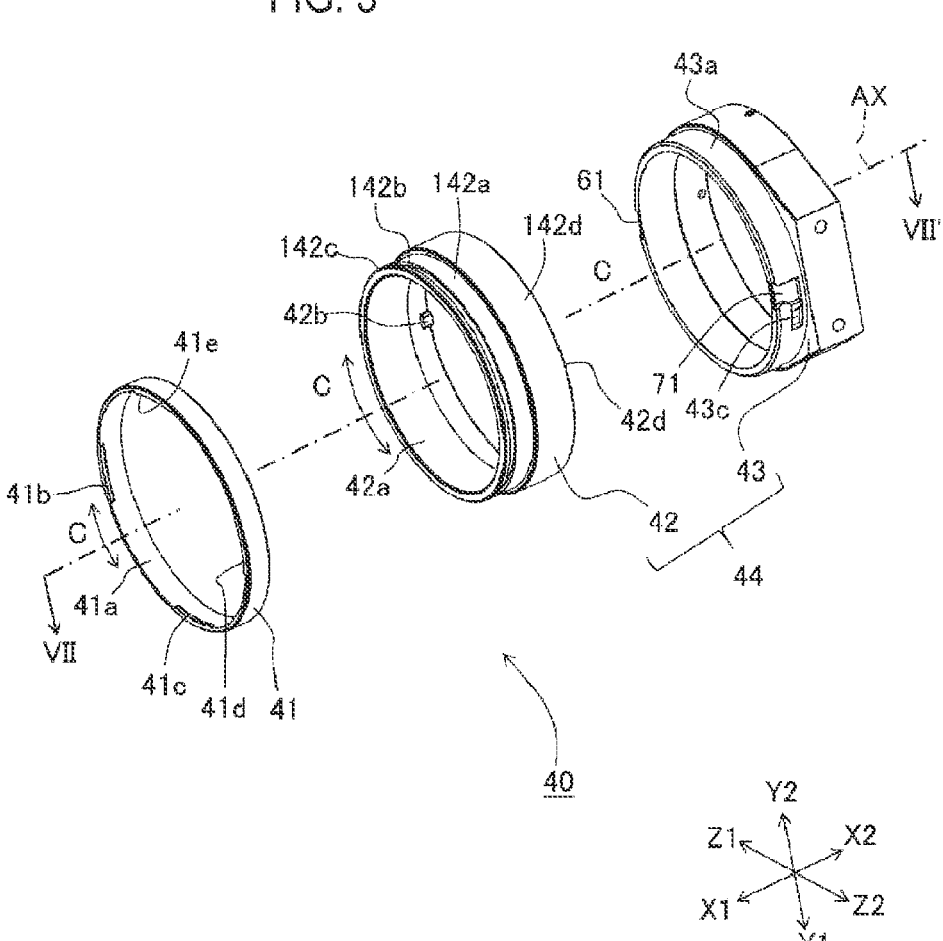
FIG. 3 is an exploded perspective view illustrating a configuration of a bearing structure according to some embodiments.

FIG. 1 is a perspective view illustrating an external configuration of a holding body of a medical robot including a bearing structure according to some embodiments. FIG. 2 is an exploded perspective view illustrating a schematic configuration of the holding body of FIG. 1, according to some embodiments. FIG. 3 is an exploded perspective view illustrating the configuration of a bearing structure according to some embodiments.

The medical robot according to some embodiments may include an arm unit that can change its direction and angle, and a holding body 10 illustrated in FIG. 1 is provided at the tip of the arm unit. From the front end of the holding body 10, a holder 21 and a separator 22 that is arranged so as to cover the holder 21 extend frontward. An insertion member inserted into the patient's body to be treated by the medical robot is detachably attached with respect to the holder 21 by using the separator 22. The posture of the insertion member is changed in accordance with the changes of the direction and angle of the arm unit. Examples of the insertion member include a treatment tool and an endoscope used for the treatment. But embodiments are not limited thereto.

As illustrated in FIG. 2, the holder 21 and the separator 22 are attached to the holding body 10 via a switch structure 31, a bearing structure 40, and a bearing member 32 that are arranged in this order from the front to the rear. The bearing member 32 is fixed to the holding body 10 via an annular bearing plate 33. The holder 21 and the separator 22 are provided integrally with the switch structure 31. The bearing member 32 is, for example, a rolling bearing whose outer ring is fixed to the holding body 10 and whose inner ring can rotate relative to the outer ring.

As illustrated in FIGS. 2 and 3, the bearing structure 40 includes a rotating member 41, a joint member 42, and a base member 43 that are all ring-shaped. Rear portions of the holder 21 and the separator 22 are inserted inside the above members of the bearing structure 40, and the holder 21 and the separator 22 are provided integrally with the rotating member 41.

The joint member 42 and the base member 43 are detachably attached to each other by fitting and constitute a fixing member 44. The base member 43 is attached with respect to the holding body 10. The rotating member 41 is attached with respect to the joint member 42 of the fixing member 44 in a slidable manner along a circumferential direction C.

The base member 43 may be composed of a metal from the viewpoint of durability against sliding with the joint member 42, and for example, aluminum or duralumin is used.

The joint member 42 and the rotating member 41 may be composed of a resin material from the viewpoint of slidability and durability against sterilization, and for example, ABS resin, polycarbonate, and polyacetal are suitable.

By configuring the rotating member 41 and the fixing member 44 with such materials, it is possible to prevent damage when sterilizing a member with which the drape contacts and to ensure the slidability for a long period of time, and damage due to sliding over a long period of time can be reduced.

The holder 21, the separator 22, the switch structure 31, and the rotating member 41 are supported by the bearing member 32 in a rotatable manner and are driven by a motor (not illustrated) to rotate around an axis of rotation AX along the front-rear direction (X1-X2 direction).

Figures 8A, 8B:
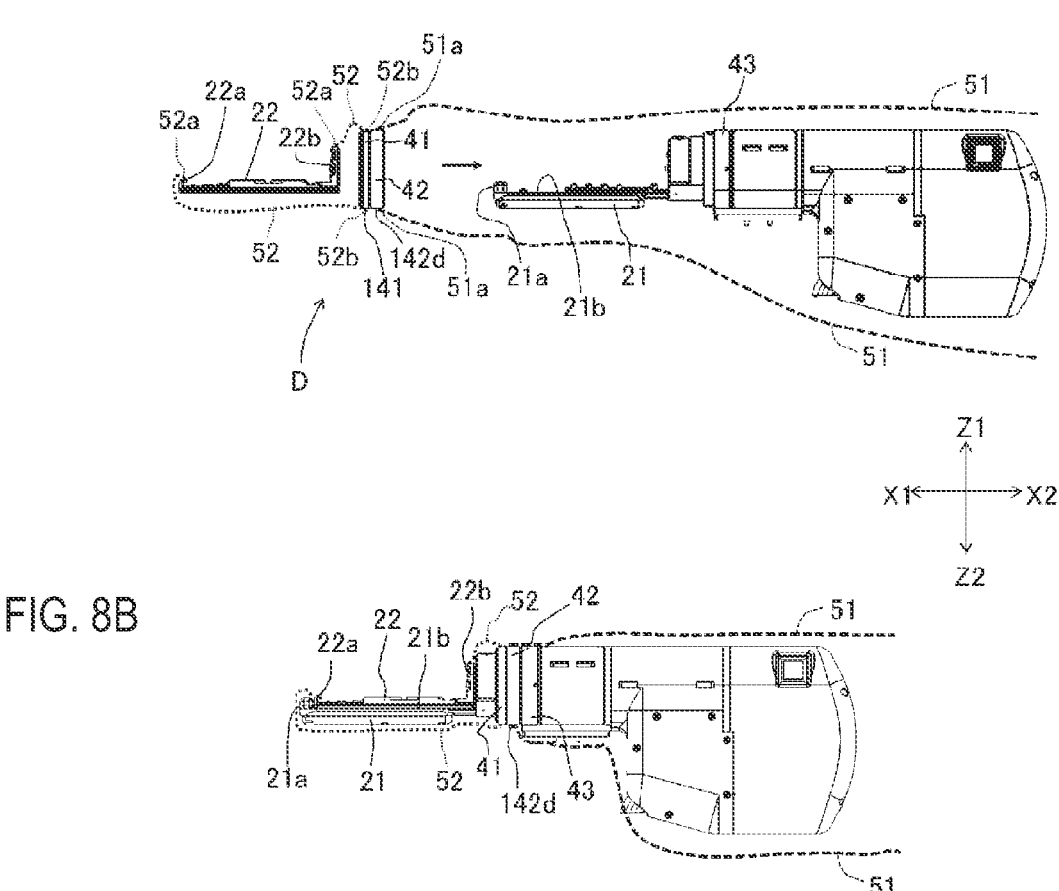
FIGS. 8A and 8B are a set of views illustrating attaching positions of a first drape and a second drape, according to some embodiments, where

As illustrated in FIGS. 8A and 8B, a front opening portion 51a of a tubular first drape 51 is fixed along an outer circumferential surface 142d on the rear side of the joint member 42 of the bearing structure 40. The first drape 51 extends rearward from the joint member 42 and covers the holding body 10 and the surgical robot including an arm unit on which the holding body 10 is provided.

The fixing member 44 includes two components of the base member 43 fixed to the holding body 10 and the joint member 42 detachable from the base member 43, and the first drape 51 can therefore be easily removed from the holding body 10 by attaching the first drape 51 to the joint member 42.

A front opening portion 52*a* of a tubular second drape 52 is provided in a linked manner with the separator 22 so as to be fixed from a front end portion 22*a* of the separator 22 to a rear end portion 22*b* of the separator 22 to cover an outer portion of the separator 22. This configuration allows the separator 22 and the second drape 52 to be integrated, and the lower surface of the separator 22 is placed in the second drape 52.

On the other hand, a rear opening portion 52*b* of the second drape 52 is fixed along an outer circumferential surface 141 of the rotating member 41.

Thus, the separator 22 and the rotating member 41 are attached with respect to the holding body 10 from the state in which the second drape 52 is attached. In this operation, the holder 21 and the switch structure 31 are inserted into the rotating member 41, and the separator 22 is attached to an upper surface 21*b* of the holder 21. According to this step, as illustrated in FIG. 8B, the front surface and lower surface of the holder 21 are covered with the second drape 52 from a front end portion 21*a* located on the front side of the front end portion 22*a* of the separator 22, and the upper surface 21*b* is covered with the separator 22. When the rotating member 41 rotates relative to the fixing member 44, the second drape 52 rotates integrally with the rotating member 41, the separator 22, and the holder 21.

(Fixing Member)

As described above, the fixing member 44 includes the joint member 42 and the base member 43. The joint member 42 has an inner circumferential surface 42*a* provided with two fitting protrusions 42*b* and 42*c* (see FIGS. 3 and 11A) while the base member 43 has an outer circumferential surface 43*a* provided with two fitting recesses 43*b* and 43*c* (see FIGS. 3, 5A, and 5B) on the joint member 42 side (X1 side, front side). The joint member 42 and the base member 43 are detachably fitted to each other by fitting the fitting protrusions 42*b* and 42*c* into the fitting recesses 43*b* and 43*c*, respectively. In this fitting, two side surfaces of each of the fitting protrusions 42*b* and 42*c* (two surfaces facing each other in the front-rear direction) and two inner side surfaces of each of the fitting recesses 43*b* and 43*c* (two inner surfaces facing each other in the front-rear direction) come into contact with each other thereby to maintain the fixed state. In this fitting state, the joint member 42 covers the outside of the base member 43 in the fitting portion, and the first drape 51 is attached to the joint member 42 as described above; therefore, in the fixing member 44, the joint member 42 and the base member 43 can be fitted to each other in a state in which a clean component covers an unclean component.

Figures 4A, 4B:
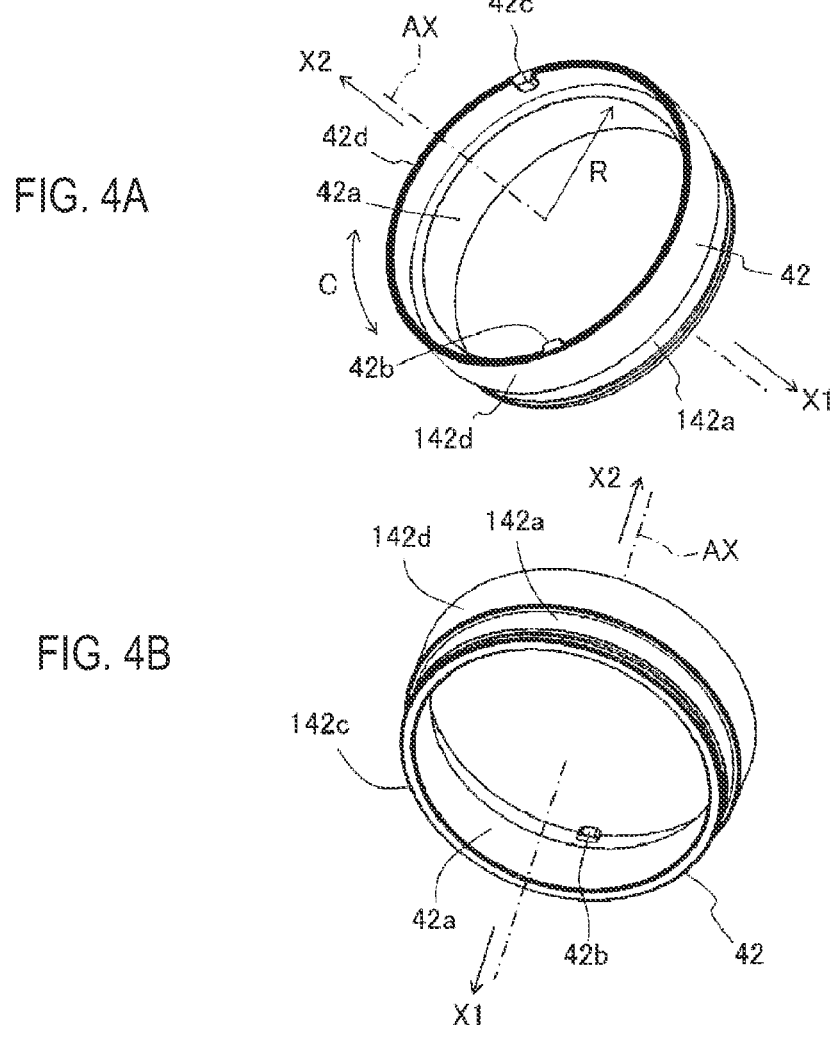
FIGS. 4A and 4B are perspective views of a configuration of a joint member as viewed from different directions, according to some embodiments.

As illustrated in FIGS. 4A and 4B, the two fitting protrusions 42*b* and 42*c* are provided at the rearmost end of the joint member 42 in the front-rear direction (X1-X2 direction). The two fitting protrusions 42*b* and 42*c* are formed so as to protrude inward (toward the axis of rotation AX side) at positions symmetrical with respect to the axis of rotation AX in the circumferential direction C of the ring-shaped joint member 42.

Figures 5A, 5B:
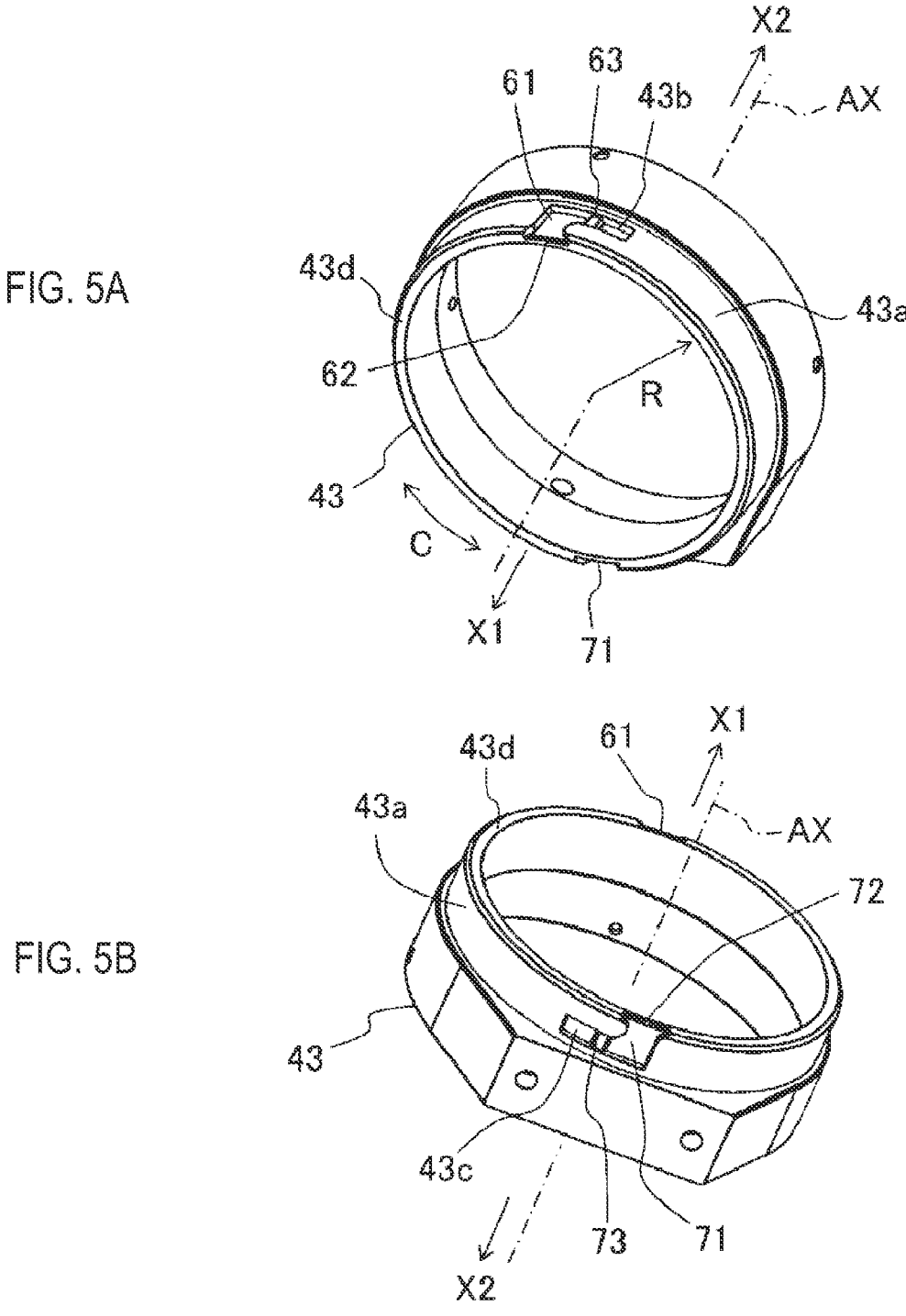
FIGS. 5A and 5B are perspective views of a configuration of a base member as viewed from different directions, according to some embodiments.

The two fitting recesses 43*b* and 43*c* are formed so as to extend along the circumferential direction C at positions symmetrical with respect to the axis of rotation AX in the circumferential direction C of the ring-shaped base member 43 (see FIGS. 3, 5A, and 5B).

As illustrated in FIG. 5A, the fitting recesses 43*b* and 43*c* are provided in a linked manner with guide grooves 61 and 71, respectively. One guide groove 61 extends rearward from the foremost end (end portion on the fitting side with the joint member 42) in the front-rear direction of the base member 43, that is, in the main axis direction which is the axial direction of the fixing member 44 and the rotating member 41. The guide groove 61 further extends along the circumferential direction C from the position corresponding to the fitting recess 43*b* in the front-rear direction. The other guide groove 71 also extends rearward from the foremost end (end portion on the fitting side with the joint member 42) in the front-rear direction of the base member 43 and further extends in the circumferential direction C from the position corresponding to the fitting recess 43*c*. Thus, when viewed along a radial direction R of the base member 43, the guide grooves 61 and 71 are both formed so as to bend in an L shape.

The fitting protrusions 42*b* and 42*c* are provided symmetrically in the circumferential direction C of the joint member 42 while the fitting recesses 43*b* and 43*c* are also provided symmetrically in the circumferential direction C of the base member 43, and therefore one of the two fitting protrusions 42*b* and 42*c* corresponds to one of the two fitting recesses 43*b* and 43*c*, and the other fitting protrusion and the other fitting recess correspond to each other. Thus, one pair of fitting protrusions and one pair of fitting recesses are provided in the circumferential direction C of the fixing member 44. For this reason, when the joint member 42 and the base member 43 are fitted together, the joint member 42 and the base member 43 can be easily moved along the axis of rotation AX, and it is therefore possible to prevent the joint member 42 and the base member 43 from biting and damaging each other during the fitting and prevent the inner surfaces of the fitting recesses from being scraped due to the slanting of the fitting protrusions.

One fitting recess 43*b* and the guide groove 61 provided in a linked manner with the fitting recess 43*b* will then be described in detail. The other fitting recess 43*c* and the guide groove 71 provided in a linked manner with the fitting recess 43*c* have symmetrical shapes to those of the fitting recess 43*b* and the guide groove 61 with respect to the axis of rotation AX, so the detailed description thereof will be omitted for conciseness.

Figure 6:
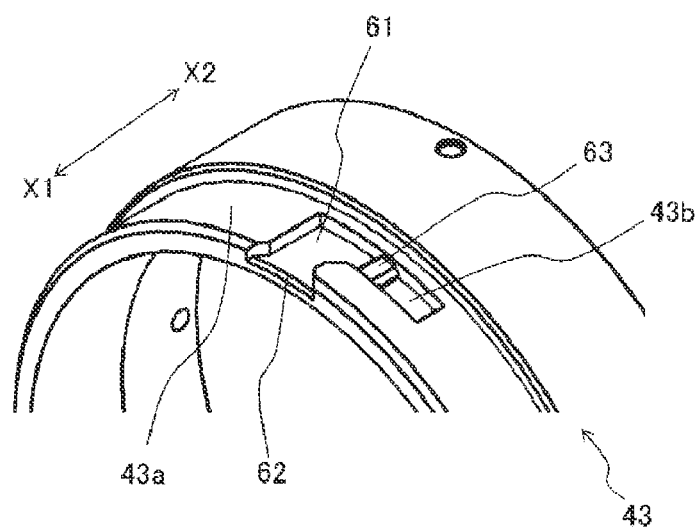
FIG. 6 is an enlarged perspective view illustrating a fitting recess of the base member and its periphery, according to some embodiments.

As illustrated in FIG. 6, the guide groove 61 provided in a linked manner with the fitting recess 43*b* has a tapered portion 62 that increases its thickness so as to reduce the depth of the guide groove 61 as the guide groove 61 extends along the main axis direction (X1-X2 direction) from the end portion on the fitting side with the joint member 42. By providing the tapered portion 62, it becomes easy to guide the fitting protrusion (either the fitting protrusion 42*b* or 42*c*) into the guide groove 61.

The guide groove 61 is provided in a linked manner with the fitting recess 43*b* via a restriction protrusion 63 in the circumferential direction C. The restriction protrusion 63 has approximately the same thickness as that of the outer circumferential surface 43*a* on the front side of the base member 43 and is provided so that the outer surface of the restriction protrusion 63 is located outside both the fitting recess 43*b* and the guide groove 61 in the radial direction R. This configuration allows the fitting protrusion (either fitting protrusion 42*b* or 42*c*) fitted in the fitting recess 43*b* to come into contact with the side surface of the restriction protrusion 63 in the circumferential direction C, so that the fitting protrusion is restricted from returning to the guide groove 61. Thus, the rotational movement of the joint member 42 with respect to the base member 43 is restricted by the restriction protrusion 63, and a trouble is therefore less likely to occur that the fitting is disengaged due to the rotational movement of the rotating member 41 attached to the joint member 42.

By providing the restriction protrusions 63 and 73, when the joint member 42 and the base member 43 are fitted to each other and the fitting is released, click feeling (attaching feeling or detaching feeling) can be given to the operator in the operation of getting across the restriction protrusions 63 and 73. Hence, even in a situation in which it is difficult to visually recognize the joint member 42 or the base member 43 due to the presence of the drape, the completion of attachment/detachment can be easily confirmed.

The guide groove 61 is formed to have wider widths than those of the fitting recess 43b in the main axis direction (X1-X2 direction) and the circumferential direction C. In other words, the guide groove 61 is formed to have wider widths than those of the fitting protrusion 42b in the main axis direction and the circumferential direction C. This configuration allows the fitting protrusion 42b to be easily guided into the guide groove 61. Moreover, in the guide groove 61, the fitting protrusion 42b comes into contact with the rear end wall in the guide groove 61 to allow for easy positioning in the main axis direction, and from this state, the fitting protrusion 42b is moved along the circumferential direction C thereby to be easily and reliably guided into the fitting recess 43b.

Also in the guide groove 71, a tapered portion 72 and a restriction protrusion 73 are provided in a similar manner to the tapered portion 62 and restriction protrusion 63 of the guide groove 61 (see FIG. 5B).

Figures 7A, 7B:
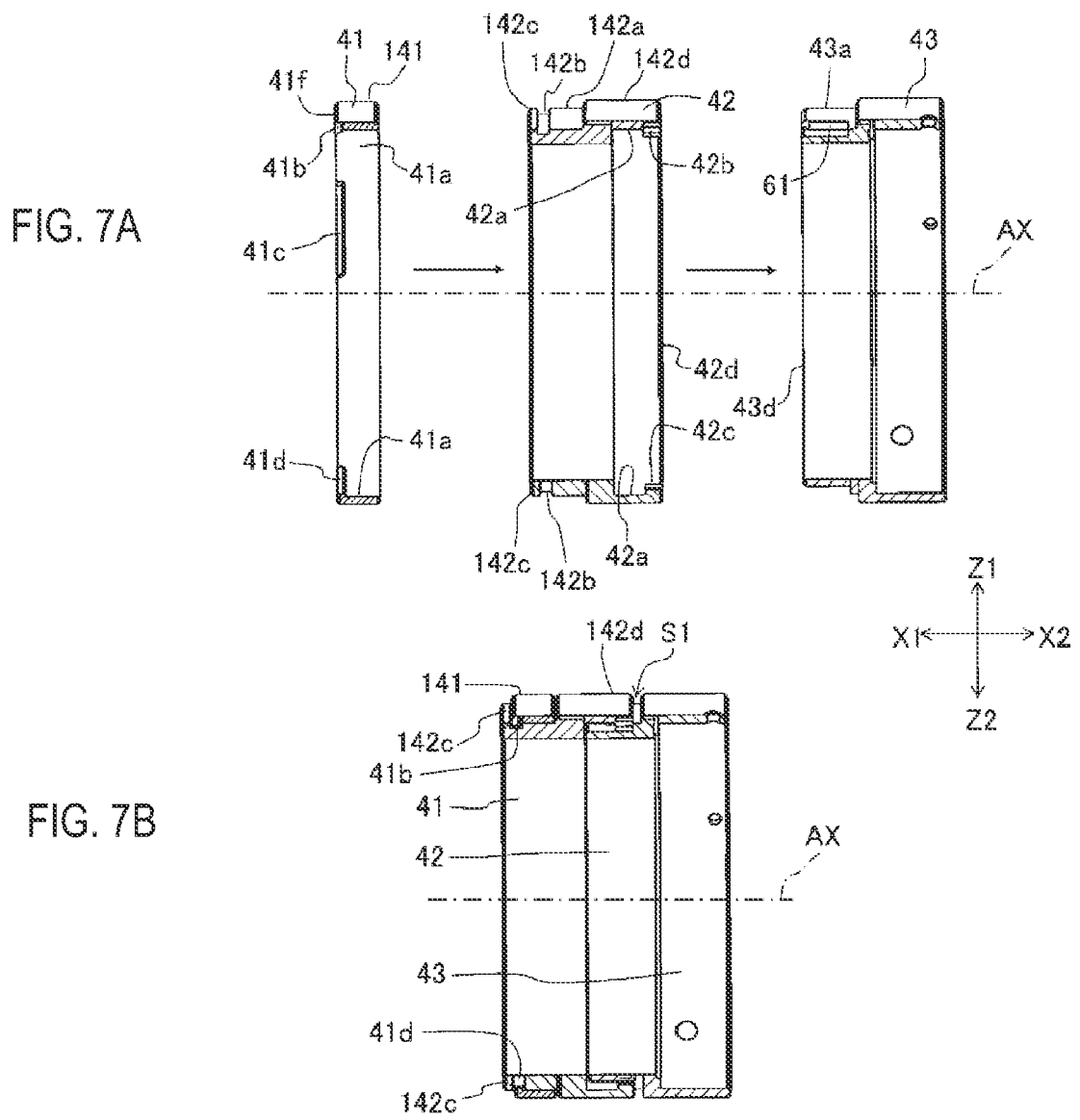
FIG. 7A is a cross-sectional view taken along the line VII-VII' of FIG. 3
FIG. 7B is a cross-sectional view illustrating a state in which the rotating member, joint member, and base member illustrated in FIG. 7A are assembled, according to some embodiments.

As illustrated in FIGS. 3 and 7A, the joint member 42 has a groove portion 142b and a protruding edge portion 142c on an outer circumferential surface 142a on the rotating member 41 side (X1 side). The protruding edge portion 142c is provided at the front end portion of the outer circumferential surface 142a in a flange shape extending outward in the radial direction R. The groove portion 142b is provided in a linked manner with the protruding edge portion 142c to have an annular shape behind the protruding edge portion 142c on the outer circumferential surface 142a, and is provided so as to be recessed inward in the radial direction R from the outer circumferential surface 142a.

Figures 10A, 10B:
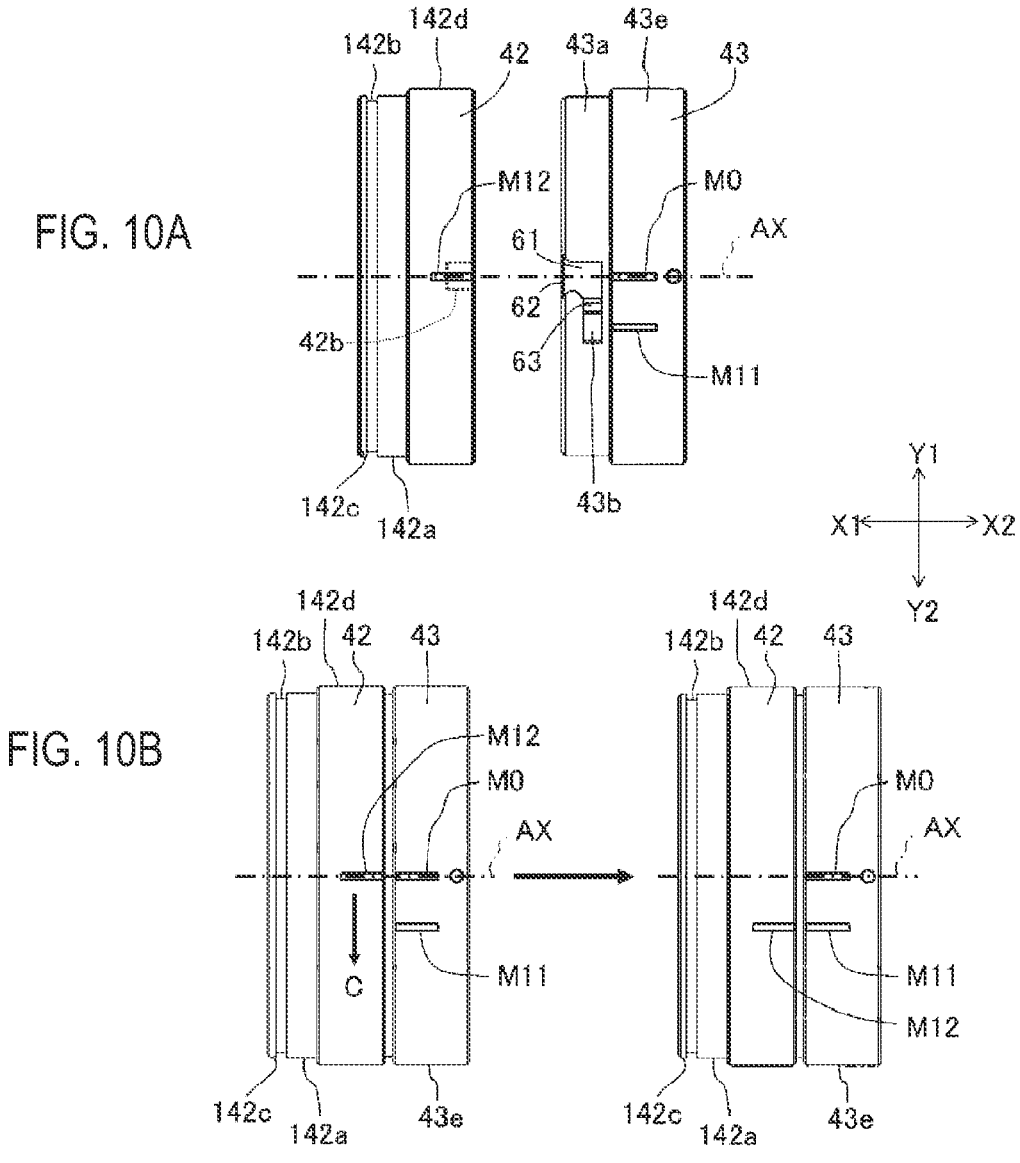
FIG. 10A is a plan view of the configurations of fitting markers and an initial position marker as viewed from above and FIG. 10B is a plan view illustrating the positions of the fitting markers and initial position marker before and after fitting of the joint member and the base member, according to some embodiments.

As illustrated in FIG. 10A, the base member 43 has a rear-side outer circumferential surface 43e, on which an initial position marker M0 is provided at a position corresponding to the center of the guide groove 61 in the left-right direction (Y1-Y2 direction) so as to extend in the front-rear direction. The initial position marker M0 corresponds to the position at which the fitting protrusion 42b is introduced into the guide groove 61. The above outer circumferential surface 43e is provided with a fitting marker M11 so as to extend in the front-rear direction at a position corresponding to the center of the fitting recess 43b in the left-right direction.

On the other hand, the joint member 42 has a rear-side outer circumferential surface 142d, on which a fitting marker M12 is provided at a position corresponding to the center of the fitting protrusion 42b in the left-right direction so as to extend in the front-rear direction. The fitting marker M12 of the joint member 42 and the fitting marker M11 of the base member 43 are arranged at the same position as each other in the circumferential direction C of the fixing member 44

(see the right figure of FIG. 10B) when the fitting protrusion 42b has reached a position at which it is fitted into the fitting recess 43b.

By providing the fitting markers M11 and M12 and the initial position marker M0, when the joint member 42 and the base member 43 are fitted to each other and the fitting is released, confirmation of the fitting and its release can be reliably performed by the visual sense in addition to the click feeling due to getting across the restriction protrusions 63 and 73, and it is therefore possible to prevent a situation in which the fitting between the joint member 42 and the base member 43 is incomplete, etc.

The initial position marker M0 and the two fitting markers M11 and 12 are provided in a linear shape having a predetermined width in each of the front-rear direction and the circumferential direction C, but embodiments are not limited thereto and, in some embodiments, other shapes may be adopted, provided that the fitting marker M12 of the joint member 42 can be reliably aligned with the initial position marker M0 or fitting marker M11 of the base member 43. In some embodiments, the markers may be formed by printing or the like or formed as recesses or protrusions on the surface to be formed with the markers, which may be preferred because the operator can sense the markers by tactile sense.

(Rotating Member)

Figures 9A, 9B:
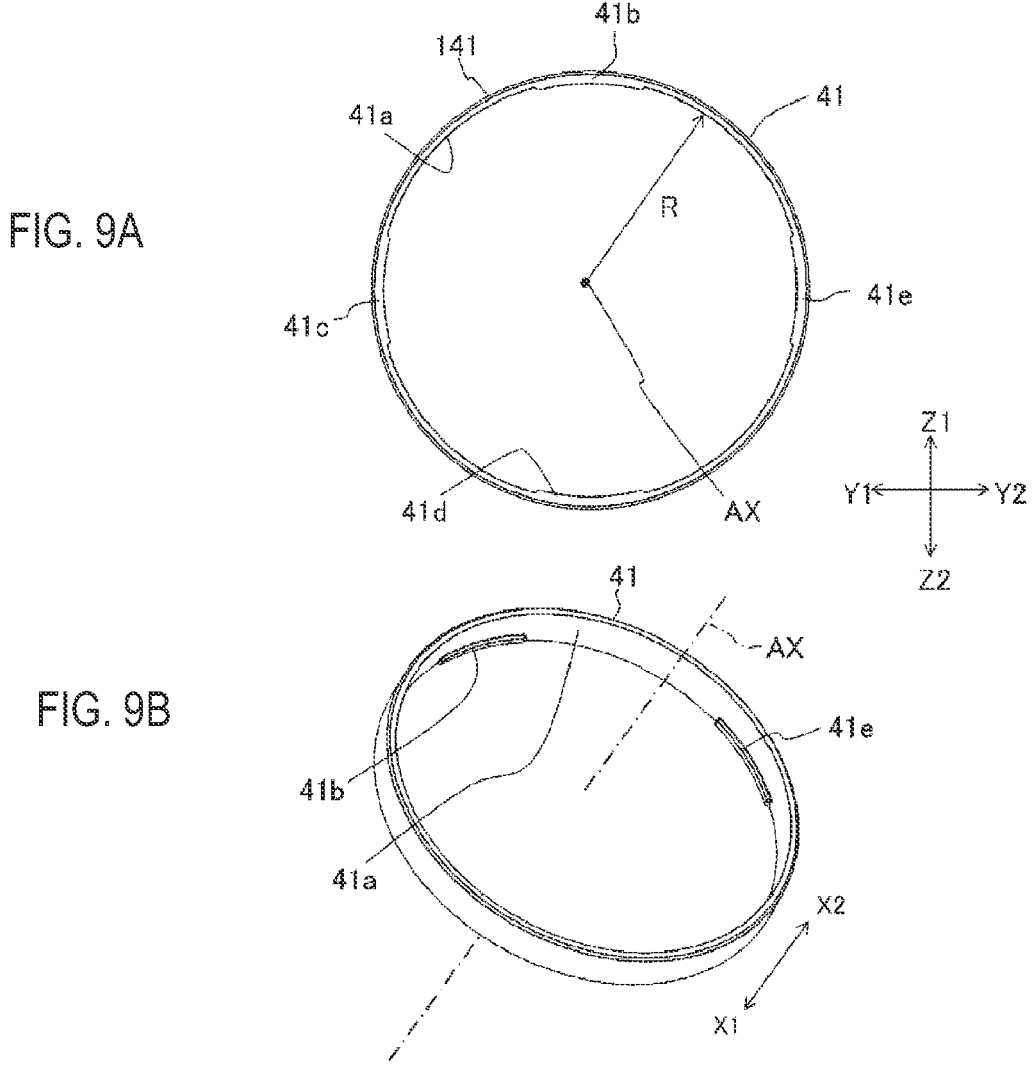
FIGS. 9A and 9B are a set of views illustrating the configuration of a rotating member, according to some embodiments, where

As illustrated in FIGS. 3, 9A, and 9B, the rotating member 41 has four tongue portions 41b, 41c, 41d, and 41e at the front end portion of an inner circumferential surface 41a. The four tongue portions 41b, 41c, 41d, and 41e are provided at identical angular intervals with respect to the axis of rotation AX, which is the central axis of the ring-shaped rotating member 41, and are provided so as to protrude inward from the inner circumferential surface 41a. When the rotating member 41 is fitted to the joint member 42, the four tongue portions 41b, 41c, 41d, and 41e are movable in the circumferential direction C in the groove portion 142b of the joint member 42 and come into contact with the protruding edge portion 142c thereby to restrict the movement in the front-rear direction. The groove portion 142b of the joint member 42 has a depth sufficient to prevent the tongue portions 41b, 41c, 41d, and 41e from coming off (Assembly of Fixing Member and Fitting of Fixing Member and Rotating Member)

The base member 43 is fixed to the outer ring of the bearing member 32 thereby to be fixed to the holding body 10.

The joint member 42 is then moved in the front-rear direction so as to cover the outer circumferential surface 43a on the front side of the base member 43. At this time, in the circumferential direction C, the initial position marker M0 on the base member 43 and the fitting marker M12 on the joint member 42 are arranged so as to coincide with each other (left figure of FIG. 10B), and the fitting protrusions 42b and 42c move in the front-rear direction while sliding in the corresponding guide grooves 61 and 71 in the base member 43 along the front-rear direction and reach the positions on the rearmost side (X2 side) in the guide grooves 61 and 71. Subsequently, the joint member 42 is rotated in the circumferential direction C until the fitting marker M12 of the joint member 42 coincides with the fitting marker M11 of the base member 43 (position at which the fitting protrusion 42b is fitted into the fitting recess 43b) (right figure of FIG. 10B). This configuration allows the fitting protrusions 42b and 42c to be moved from the guide grooves 61 and 71 into the fitting recesses 43b and 43c beyond the restriction protrusions 63 and 73 and fitted into the fitting recesses 43b and 43c. Through this series of operations, the joint member 42 and the base member 43 are fitted to each other, and the movement of the joint member 42 with respect to the base member 43 is restricted in the front-rear direction (main axis direction) and the circumferential direction C.

On the other hand, in the release of fitting between the joint member 42 and the base member 43, the joint member 42 is rotated by the force larger than a predetermined value in the circumferential direction opposite to that when the joint member 42 is fitted with respect to the base member 43. Then, when the fitting protrusions 42b and 42c get across the restriction protrusions 63 and 73 and the fitting marker M12 of the joint member 42 reaches a position corresponding to the initial position marker M0 of the base member 43, the fitting protrusions 42b and 42c are released from the fitting recesses 43b and 43c, respectively, and the joint member 42 can therefore be removed from the base member 43. The above predetermined value is appropriately set in accordance with the spec of the surgical robot and the like.

Here, the fitting protrusions 42b and 42c share a plane on which their rear end surfaces are orthogonal to the extending direction of the axis of rotation AX (main axis), and this plane is flush with a rear end surface 42d of the joint member 42 (see FIGS. 4A and 7). In other words, a part of the rear end surface 42d of the joint member 42 constitutes each of the rear end surfaces of the fitting protrusions 42b and 42c, and other parts form non-fitting regions that do not fit to the fitting recess 43b or 43c of the base member 43. With such a configuration, when the joint member 42 is fitted with respect to the base member 43, even in a state in which the fitting protrusions 42b and 42c and the fitting recesses 43b and 43c do not face each other in the axial direction, at least one of the joint member 42 and the base member 43 can be easily guided to a position at which the fitting protrusions 42b and 42c and the fitting recesses 43b and 43c correspond to each other through bringing the rear end surface 42d of the joint member 42 and a front end surface 43d of the base member 43 into contact with each other and sliding them along the circumferential direction C.

The rotating member 41 is attached with respect to the joint member 42 before it is fitted to the base member 43. The rotating member 41 is attached with respect to the joint member 42 by being moved along the front-rear direction so as to cover the outer circumferential surface 142a on the front side of the joint member 42 with the inner circumferential surface 41a (see FIGS. 10A and 10B). In this attaching, the tongue portions 41b, 41c, 41d, and 41e of the rotating member 41 are engaged in the groove portion 142b of the joint member 42, and the rotating member 41 is thereby attached to the joint member 42 in a state of being rotatable around the axis of rotation AX.

In the above assembly process, before the joint member 42 to which the rotating member 41 is fixed is fitted to the base member 43 (state of FIG. 8A), the front opening portion 51a of the first drape 51 is fixed to the outer circumferential surface 142d on the rear side of the joint member 42, such as by adhesion, and the rear opening portion 52b of the second drape 52 is fixed with respect to the outer circumferential surface 141 of the rotating member 41, such as by adhesion. The front opening portion 52a of the second drape 52 is fixed with respect to the front end portion 22a and rear end portion 22b of the separator 22. By fixing the first drape 51 and the second drape 52 in this way, a drape unit D is configured to include the bearing structure 40, which includes the rotating member 41, the joint member 42, and the base member 43, the first drape 51 attached to the fixing member 44, the second drape 52 attached to the separator 22 and the rotating member 41, and the separator 22 which covers the holder 21 from above.

As illustrated in FIG. 7B, a gap S1 is formed between the joint member 42 and the base member 43 along the circumferential direction C in the front-rear direction (direction along the axis of rotation AX). In the front-rear direction, the length of the gap S1 is twice or more the thickness of the first drape 51. By providing the gap S1 with such a size, when the joint member 42 is fitted with respect to the base member 43 in a state in which the first drape 51 is fixed to the joint member 42, a trouble of tucking the first drape 51 into the gap S1 is less likely to occur.

Through the above steps, the holder 21, the separator 22, the switch structure 31, the rotating member 41, the fixing member 44, the bearing member 32, and the bearing plate 33 are attached with respect to the holding body 10. Here, the fixing member 44 is fixed to the holding body 10. On the other hand, the rotating member 41 can rotate relative to the fixing member 44 around the axis of rotation AX. The rotating member 41 is integrated with the holder 21 and the separator 22, which are rotatable together with the inner ring of the bearing member 32, and can rotate around the axis of rotation AX.

This configuration allows the separator 22 whose relative position is fixed with respect to the holder 21 to rotate as the holder 21 rotates, and even when the second drape 52 rotates accordingly, the rotating member 41 to which the second drape 52 is attached rotates relative to the fixing member 44. Therefore, the fixing member 44 to which the first drape 51 is attached does not rotate, and even if the holder 21 rotates beyond 360 degrees, the first drape 51 is less likely to be twisted, and the damage of the first drape 51 can be prevented.

Moreover, the guide groove 71 is formed to have an L shape when viewed along the radial direction R by extending the guide groove 71 along the main axis direction from the fitting side end portion in the main axis direction (direction in which the axis of rotation AX extends) which is the axial direction of the fixing member 44 and the rotating member 41 and further extending the guide groove 71 along the circumferential direction C of the fixing member 44 and the rotating member 41, so that two operations in the axial direction and the circumferential direction C are performed as the fitting operation for the joint member 42 with respect to the base member 43. Therefore, the fitting is less likely to come off even if there is vibration or the like, and the fitting state is easy to stabilize.

When the rotating member 41 is attached with respect to the joint member 42, a front surface 41f of the rotating member 41 comes into contact with the protruding edge portion 142c in the main axis direction because the protruding edge portion 142c is provided on the joint member 42 of the fixing member 44. This configuration can prevent the rotating member 41 from detaching from the joint member 42, and even when the second drape 52 attached to the rotating member 41 is pulled frontward in the axial direction, for example, a problem is less likely to occur that the rotating member 41 comes off from the joint member 42 to expose the unclean portion.

Moreover, when the rotating member 41 is attached to the joint member 42, the tongue portions 41b, 41c, 41d, and 41e provided at the end portion in the axial direction of the rotating member 41 are fitted in the groove portion 142b of the joint member 42 in a state of being slidable along the circumferential direction C. This configuration allows the rotating member 41 to stably rotate along the circumferential direction C while being restricted in the movement along the axial direction.

Additional Embodiments

As described above, the joint member 42 is provided with the fitting protrusions 42b and 42c and the base member 43 is provided with the fitting recesses 43b and 43c, but embodiments are not limited to this. In some embodiments, the base member 43 may be provided with fitting protrusions and the joint member 42 may be provided with fitting recesses.

As described above, the joint member 42 is fitted from the outside of the base member 43. However, embodiments are not limited thereto. In some embodiments, the base member may be fitted from the outside of the joint member.

Figures 11A, 11B:
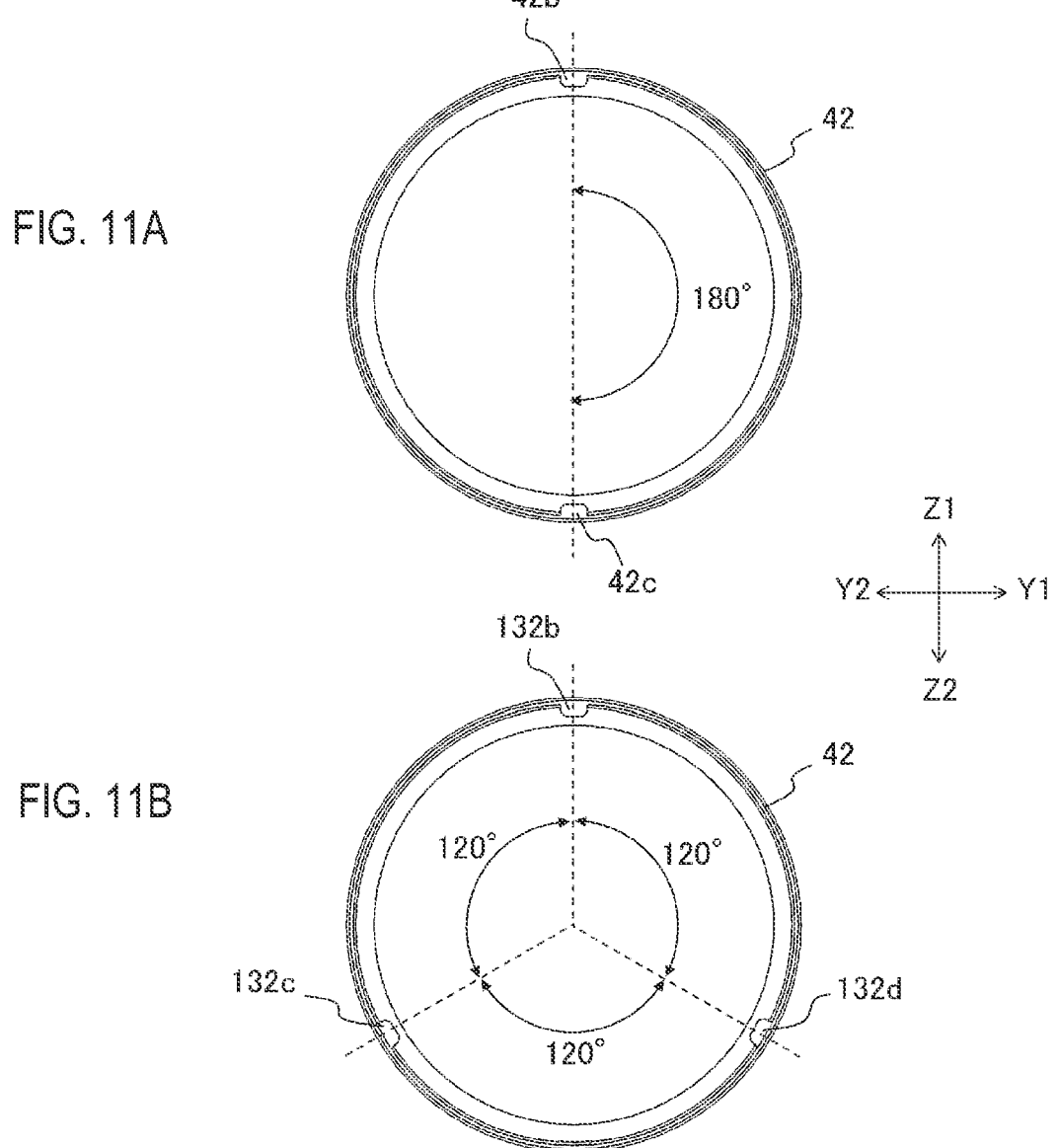
FIG. 11A is a rear view illustrating the configuration of the joint member and FIG. 11B is a rear view illustrating the configuration of a joint member, according to some embodiments.

As described above, the two fitting protrusions 42b and 42c and the two fitting recesses 43b and 43c are provided at equal angle intervals of 180 degrees when viewed along the main axis direction (X1-X2 direction). FIG. 11A illustrates the fitting protrusions 42b and 42c provided on the joint member 42. However, embodiments are not limited thereto.

In some embodiments, three or more pairs of fitting protrusions and fitting recesses may be provided. Three or more pairs can stabilize the fitting state when fitting the fixing member 44 and the rotating member 41 to each other, and the fitting protrusions can therefore be easily fitted into the fitting recesses. FIG. 11B illustrates an example in which the joint member 42 is provided with three fitting protrusions 132b, 132c, and 132d at equal angle intervals of 120 degrees. In the case of this configuration, the fitting recesses are also provided so as to correspond to the fitting protrusions 132b, 132c, and 132d at equal angle intervals of 120 degrees. With this configuration, in the process of fitting the joint member 42 to the base member 43, when they are subjected to relative rotation while bringing the front end surface 43d of the base member 43 into contact with the three fitting protrusions 132b, 132c, and 132d, the presence of the three fitting protrusions can stabilize the rotation and can also efficiently and reliably transmit the force required for fitting the base member 43 and the joint member 42 to each other.

In the example illustrated in FIG. 11B, the three fitting protrusions 132b, 132c, and 132d are provided at equal angle intervals of 120 degrees, but if the three fitting protrusions 132b, 132c, and 132d are distributed, for example, at 110 degrees, 140 degrees, and 110 degrees rather than setting equal angle intervals of the fitting protrusions, the attachment is possible only at determined positions in the circumferential direction, and it is therefore possible to prevent the drape from being attached in a twisted state when fitting the fitting protrusions and the fitting recesses to each other.

Such a configuration in which the angle intervals are not the same is advantageous because the same effect can be obtained also when applied to a configuration in which two fitting protrusions and two fitting recesses are provided. Specific examples of such cases include those in which the angle intervals between the fitting protrusions and between the fitting recesses are set to 170 degrees and 190 degrees.

Figure 12:
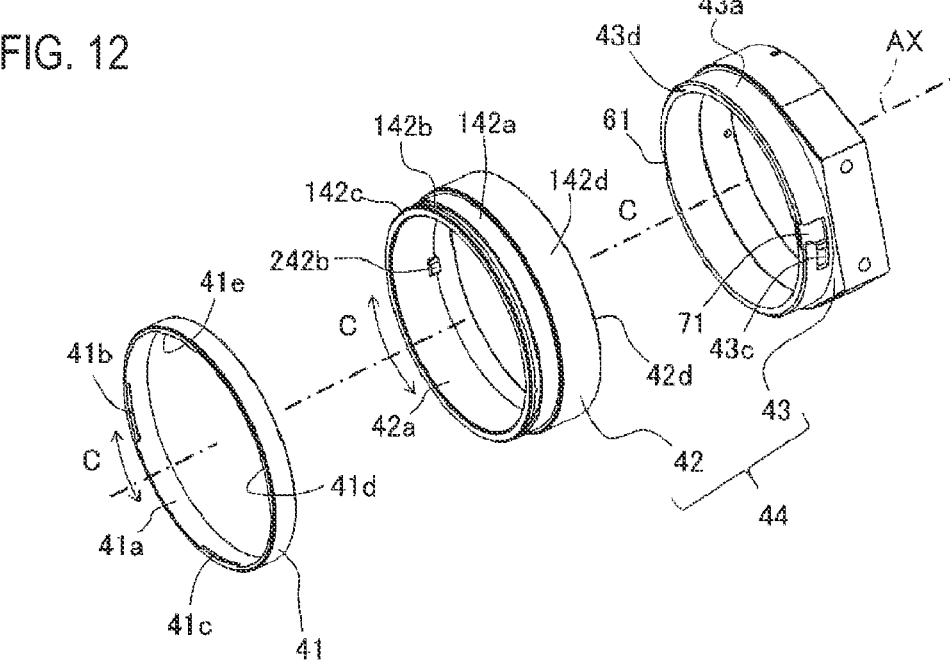
FIG. 12 is an exploded perspective view illustrating a configuration of a bearing structure, according to some embodiments.

As described above, the fitting protrusion 42b is disposed at a position at which its rear end surface is flush with the rear end surface 42d of the joint member 42, but embodiments are not limited to this. In some embodiments, as illustrated in FIG. 12, a fitting protrusion 242b may be disposed at a position at a predetermined distance from the rear end surface 42d of the joint member 42 to the front side (X1 side) in the main axis direction. The same applies to the other fitting protrusion 42c.

When the fitting protrusion 242b is disposed so as to be shifted inward from the rear end surface 42d of the joint member 42 in this way, upon the fitting of the joint member 42 and the base member 43 to each other, at least one of the joint member 42 and the base member 43 can be easily rotated around the axis of rotation AX while maintaining a state in which the fitting protrusion 242b is in contact with a non-fitting region on the front end surface 43d of the base member 43. The fitting protrusion 242b can therefore be easily guided to the guide groove 61 or 71 of the base member 43.

As described above, the fitting protrusions 42b and 42c and the fitting recesses 43b and 43c are arranged symmetrically with respect to the axis of rotation AX in the circumferential direction C, and fitting at two positions is possible. However, embodiments are not limited to this. In some embodiments, the fitting protrusions and the fitting recesses may be arranged asymmetrically, and the intervals may be different between clockwise and counterclockwise in the circumferential direction C. When three or more fitting protrusions and three or more fitting recesses are provided, an arrangement may be adopted in which at least a part or some of the intervals are not the same as the other intervals. With such an arrangement, the fitting position of the joint member 42 and the base member 43 in the circumferential direction C is fixed to one, and the orientation of the separator 22 can therefore be easily adjusted.

As described above, the surface shape of the fitting protrusions 42b and 42c is a shape corresponding to the bottom surface shape of the fitting recesses 43b and 43c. That is, when the bottom surface of the fitting recesses 43b and 43c is a curved surface having the same curvature as that of the outer circumferential surface 43a on the front side, a curved surface facing thereto is adopted, while when the bottom surface of the fitting recesses 43b and 43c is a flat surface, a flat surface facing thereto is adopted. However, embodiments are not limited to this.

Figure 13:
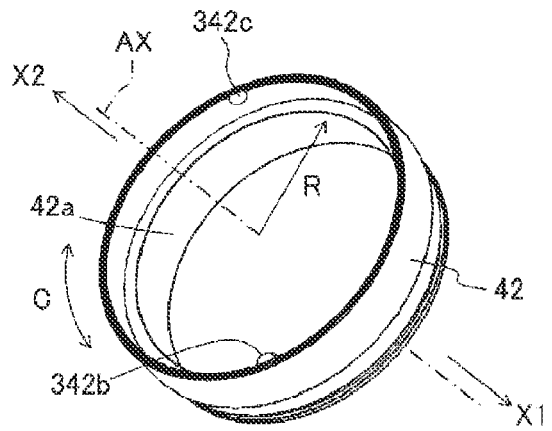
FIG. 13 is a perspective view illustrating a configuration of a joint member, according to some embodiments.

In some embodiments, the surface shape of the fitting protrusions may be a hemispherical shape protruding along the radial direction R (shape of fitting protrusions 342b and 342c in FIG. 13), and the inner surface shape of the fitting recesses may be a recessed shape corresponding to the above hemispherical shape. In some embodiments, instead of the fitting recesses 43b and 43c, protrusions that hemispherically protrude outward in the radial direction R may be provided on the outer circumferential surface 43a on the front side of the base member 43, and recesses corresponding to the shape of the above protrusions may be provided on the inner circumferential surface 42a of the joint member 42. According to these forms, workability can be improved in both the fitting of the joint member 42 and the base member 43 to each other and the release of the fitting, and the protrusions and the recesses can be easily processed.

Figure 14:
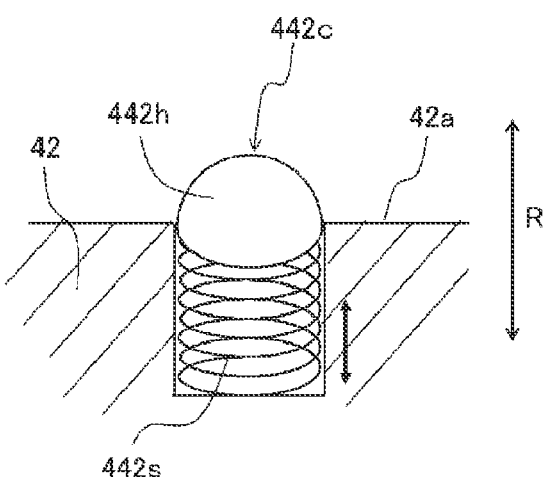
FIG. 14 is a cross-sectional view conceptually illustrating a configuration of a fitting protrusion, according to some embodiments.

In some embodiments, as illustrated in FIG. 14, a fitting protrusion 442c may be configured to include a spherical portion 442h and a biasing portion 442s that biases the spherical portion 442h outward from the inner circumferential surface 42a, that is, in a direction toward the axis of rotation AX in the radial direction R. In the example illustrated in FIG. 14, the spherical portion 442h is hemispherical, but it may be a sphere, while a compression spring is illustrated as the biasing portion 442s, but a spring other than the compression spring, a rubber material, or the like can also be used, provided that it can bias the spherical portion 442h along the radial direction R. With such a configuration, it is not necessary to control the elastic deformation of the fitting recesses, and damage to the fitting recesses can be reduced.

While various embodiments have been described, the present disclosure is not limited to the above embodiments and the various embodiments may be improved or modified within the scope of the present disclosure.

Thus, it should be understood that the present disclosure is not limited to the above embodiments, but various other changes and modifications may be made therein without departing from the spirit and scope of the appended claims.

What is claimed is:

1. A bearing structure comprising:
a fixing member attached with respect to an arm of a surgical robot in a state in which a holder that is provided at a distal end of the arm is inserted inside the fixing member, a first drape that covers the arm being attachable to the fixing member; and
a rotating member attached with respect to the fixing member in a slidably rotatable manner in a state in which the holder is inserted inside the rotating member, a second drape that covers the holder being attachable to the rotating member,
wherein the rotating member is rotatable together with the holder.

2. The bearing structure according to claim 1, wherein the fixing member and the rotating member are annular,
wherein the fixing member comprises:
a base member that is attached to the arm; and
a joint member that is configured to be fitted onto the base member and detachably attached to the base member, and
wherein the rotating member is attached to the joint member in the slidably rotatable manner.

3. The bearing structure according to claim 2, wherein the base member and the joint member are detachably fitted to each other by fitting a fitting protrusion provided on one of the base member and the joint member to a fitting recess provided in another one of the base member and the joint member.

4. The bearing structure according to claim 3, wherein the fitting protrusion is provided on an outer circumferential surface of the base member and the fitting recess is provided in an inner circumferential surface of the joint member, or the fitting protrusion is provided on the inner circumferential surface of the joint member and the fitting recess is provided in the outer circumferential surface of the base member.

5. The bearing structure according to claim 4, wherein
the fitting recess connects with a guide groove that extends along a circumferential direction of the fixing member and the rotating member, and
the fitting protrusion is moved along the guide groove to rotate and guide the fitting protrusion into the fitting recess.

6. The bearing structure according to claim 5, wherein the guide groove extends along a main axis direction from a fitting side end portion in the main axis direction and further extends in the circumferential direction of the fixing member and the rotating member, the main axis direction being an axial direction of the fixing member and the rotating member.

7. The bearing structure according to claim 6, wherein the guide groove has a tapered portion in which a depth of the guide groove decreases as the guide groove extends from an end portion of the guide groove in the main axis direction along the main axis direction.

8. The bearing structure according to claim 6, wherein:
the fitting recess comprises a plurality of fitting recesses and the fitting protrusion comprises a plurality of fitting protrusions corresponding respectively to the plurality of fitting recesses,
the plurality of fitting recesses and the plurality of fitting protrusions are provided in pairs in the circumferential direction, and
the plurality of fitting protrusions are provided at positions at a predetermined distance in the main axis direction from the fitting side end portion in the main axis direction.

9. The bearing structure according to claim 5, wherein the guide groove is formed to have a wider width than a width of the fitting recess in a main axis direction that is an axial direction of the fixing member and the rotating member.

10. The bearing structure according to claim 5, wherein the guide groove is connected to the fitting recess via a restriction protrusion, and the restriction protrusion restricts the fitting protrusion that has been fitted into the fitting recess from returning to the guide groove.

11. The bearing structure according to claim 5, wherein the base member and the joint member are provided with respective fitting markers that indicate that the fitting protrusion has reached a position at which the fitting protrusion is fitted into the fitting recess by rotating the joint member relative to the base member.

12. The bearing structure according to claim 11, wherein the fitting marker provided on the base member and the fitting marker provided on the joint member are arranged at a same position as each other in the circumferential direction of the fixing member when the fitting protrusion has reached the position at which the fitting protrusion is fitted into the fitting recess.

13. The bearing structure according to claim 11, wherein the base member is provided with an initial position marker that indicates that a position in the circumferential direction of the fitting protrusion corresponds to a position of the guide groove.

14. The bearing structure according to claim 3, wherein:
the fitting recess comprises a plurality of fitting recesses and the fitting protrusion comprises a plurality of fitting protrusions corresponding respectively to the plurality of fitting recesses, and
the plurality of fitting recesses and the plurality of fitting protrusions are provided in pairs in a circumferential direction of the fixing member and the rotating member.

15. The bearing according to claim 14, wherein at least some of the fitting recesses and fitting protrusions have different intervals in the circumferential direction.

16. The bearing structure according to claim 3, wherein the fitting protrusion is hemispherical.

17. The bearing structure according to claim 3, wherein the fitting protrusion has a spherical portion and a biasing portion that biases the spherical portion in an outward direction.

18. The bearing structure according to claim 2, wherein the base member is composed of a metal, and the joint member and the rotating member are composed of a resin material having durability against sterilization.

19. The bearing structure according to claim 2, wherein:
the first drape is fixed to an outer circumferential surface of the joint member, and
when fitted together, the base member and the joint member have a gap therebetween, the gap having a length that is at least twice a thickness of the first drape in an axial direction of the fixing member and the rotating member.

20. The bearing structure according to claim 1, wherein the fixing member has a protruding edge portion at an end portion of the fixing member in an axial direction, and the protruding edge portion protrudes outward in a radial direction from the fixing member, and when the rotating member is attached to the fixing member in the slidably rotatable manner, the rotating member contacts the protruding edge portion to be prevented from being detached from the fixing member.

21. A drape unit comprising:

the bearing structure according to claim 1;

the first drape attached to the fixing member;

the second drape attached to the rotating member; and a separator that is connected to the second drape, wherein the holder detachably holds an insertion member that is adapted to be inserted into a patient during a surgery, and the separator is located between the holder and the insertion member.

22. A bearing structure comprising:

a fixing member that is attached through a bearing member to a holding body provided at a distal end of an arm of a surgical robot, the fixing member comprising an annular groove in an outer circumferential surface of the fixing member at a distal end of the fixing member, a first drape that covers the arm being attachable to the fixing member; and a rotating member that comprises a plurality of tongue protrusions that protrude radially inward at a distal end of the rotating member, a second drape being attachable to the rotating member, wherein, when the rotating member is fitted to the fixing member, the plurality of tongue protrusions engage with the annular groove such that the plurality of tongue protrusions are rotatable within the annular groove.

23. The bearing structure according to claim 22, wherein the fixing member comprises:

a base member attached to the bearing member; and a joint member that is fitted to an outer circumferential surface of the base member, the joint member having the annular groove in an outer circumferential surface of the joint member at a distal end of the joint member, the first drape being attachable to the joint member.

* * * * *